(12) United States Patent
Gigie et al.

(10) Patent No.: US 12,688,635 B2
(45) Date of Patent: Jul. 21, 2026

(54) SYSTEMS AND METHODS FOR IN BODY MICROWAVE IMAGING OF A SUBJECT

(71) Applicant: Tata Consultancy Services Limited, Mumbai (IN)

(72) Inventors: Andrew Gigie, Bengaluru (IN); Krishna Kanth Rokkam, Bengaluru (IN); Achanna Anil Kumar, Bengaluru (IN); Tapas Chakravarty, Kolkata (IN); Arpan Pal, Kolkata (IN); Anwesha Khasnobish, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 274 days.

(21) Appl. No.: 18/745,440

(22) Filed: Jun. 17, 2024

(65) Prior Publication Data

US 2024/0420387 A1 Dec. 19, 2024

(30) Foreign Application Priority Data

Jun. 19, 2023 (IN) .............................. 202321041564

(51) Int. Cl.
*G06K 9/00* (2022.01)
*A61B 5/00* (2006.01)
(Continued)

(52) U.S. Cl.
CPC ............ *G06T 12/10* (2026.01); *A61B 5/0507* (2013.01); *A61B 5/4312* (2013.01);
(Continued)

(58) Field of Classification Search
USPC ........ 382/100, 103, 106–107, 128–134, 156, 382/224, 305; 374/122; 600/407, 430
See application file for complete search history.

(56) References Cited

U.S. PATENT DOCUMENTS 6,567,688 B1 * 5/2003 Wang ................... A61B 5/0095
600/407
10,660,531 B1 * 5/2020 Libove ................... A61B 5/021
(Continued)

OTHER PUBLICATIONS

Ambrosanio, Michele et al., "An End-to-End Deep Learning Approach for Quantitative Microwave Breast Imaging in Real-Time Applications", Title of the item: Bioengineering, Date: 2022, vol. 9; Issue: 11, Publisher: MDPI, Link: http://www.mdpi.com/2306-5354/9/11/651.
(Continued)

*Primary Examiner* — Seyed H Azarian
(74) *Attorney, Agent, or Firm* — Finnegan, Henderson, Farabow, Garrett & Dunner, LLP

(57) ABSTRACT

Detecting cancer early can significantly reduce mortality rate, but this still remains a challenge owing to shortcomings in early screening and detection with existing modalities. Cancer detection is done using known screening methods such as X-ray mammography, Magnetic Resonance Imaging (MRI) and Ultrasound imaging (US). But these conventional methods have their own limitations such as compression discomfort, inherent health risks, expensive, and consume more time and effort. Present disclosure provides system and method for enhanced microwave imaging (MWI) for efficient breast tumor detection by scanning subject's specific body portion to optimize the scan duration. The MWI is framed as an inverse problem by building forward model using a Point Spread Function (PSF) and is solved by imposing sparsity prior since tumor is concentrated to limited regions. The entire scanning duration is optimized by viewing the problem as a sequential decision making process for a Deep Reinforcement Learning (DRL) agent.

18 Claims, 7 Drawing Sheets

(51) Int. Cl.

| | |
|---|---|
| *A61B 5/0507* | (2021.01) |
| *G06T 7/00* | (2017.01) |
| *G06T 11/00* | (2026.01) |
| *G06T 12/10* | (2026.01) |
| *G06T 12/20* | (2026.01) |
| *G16H 50/20* | (2018.01) |

(52) U.S. Cl.

CPC .......... *A61B 5/4842* (2013.01); *G06T 7/0012* (2013.01); *G06T 12/20* (2026.01); *G16H 50/20* (2018.01); *A61B 5/708* (2013.01); *G06T 2207/20081* (2013.01); *G06T 2207/20084* (2013.01); *G06T 2207/30068* (2013.01); *G06T 2207/30096* (2013.01); *G06T 2210/41* (2013.01); *G06T 2211/441* (2023.08)

(56) References Cited

U.S. PATENT DOCUMENTS

| | | | | |
|---|---|---|---|---|
| 11,250,601 | B2 * | 2/2022 | Chen ....................... | A61B 6/032 |
| 12,524,888 | B2 * | 1/2026 | Fasoula ................. | G06T 7/0012 |

| | | | | |
|---|---|---|---|---|
| 2014/0276031 | A1 * | 9/2014 | Lomnitz .............. | A61B 5/4312 600/430 |
| 2015/0185088 | A1 * | 7/2015 | Rabieirad .......... | A61B 5/02055 374/122 |
| 2017/0200067 | A1 | 7/2017 | Zhou et al. | |
| 2019/0336034 | A1 * | 11/2019 | Bore ...................... | A61B 5/708 |
| 2019/0391253 | A1 * | 12/2019 | Szu ...................... | A61B 5/0077 |

OTHER PUBLICATIONS

Hossain, Amran et al., "A YOLOv3 Deep Neural Network Model to Detect Brain Tumor in Portable Electromagnetic Imaging System", Title of the item: IEEE Access, Date: 2021, Publisher: IEEE, Link: https://ieeexplore.ieee.org/stamp/stamp.jsp?arnumber=9446998.

Shao, Wenyi et al., "Microwave Imaging by Deep Learning Network: Feasibility and Training Method", Title of the item: IEEE Trans Antennas Propag, Date: 2020, vol. 68; Issue: 7, Publisher: NCBI, Link: https://www.ncbi.nlm.nih.gov/pmc/articles/PMC8189033/pdf/nihms-1597149.pdf.

* cited by examiner

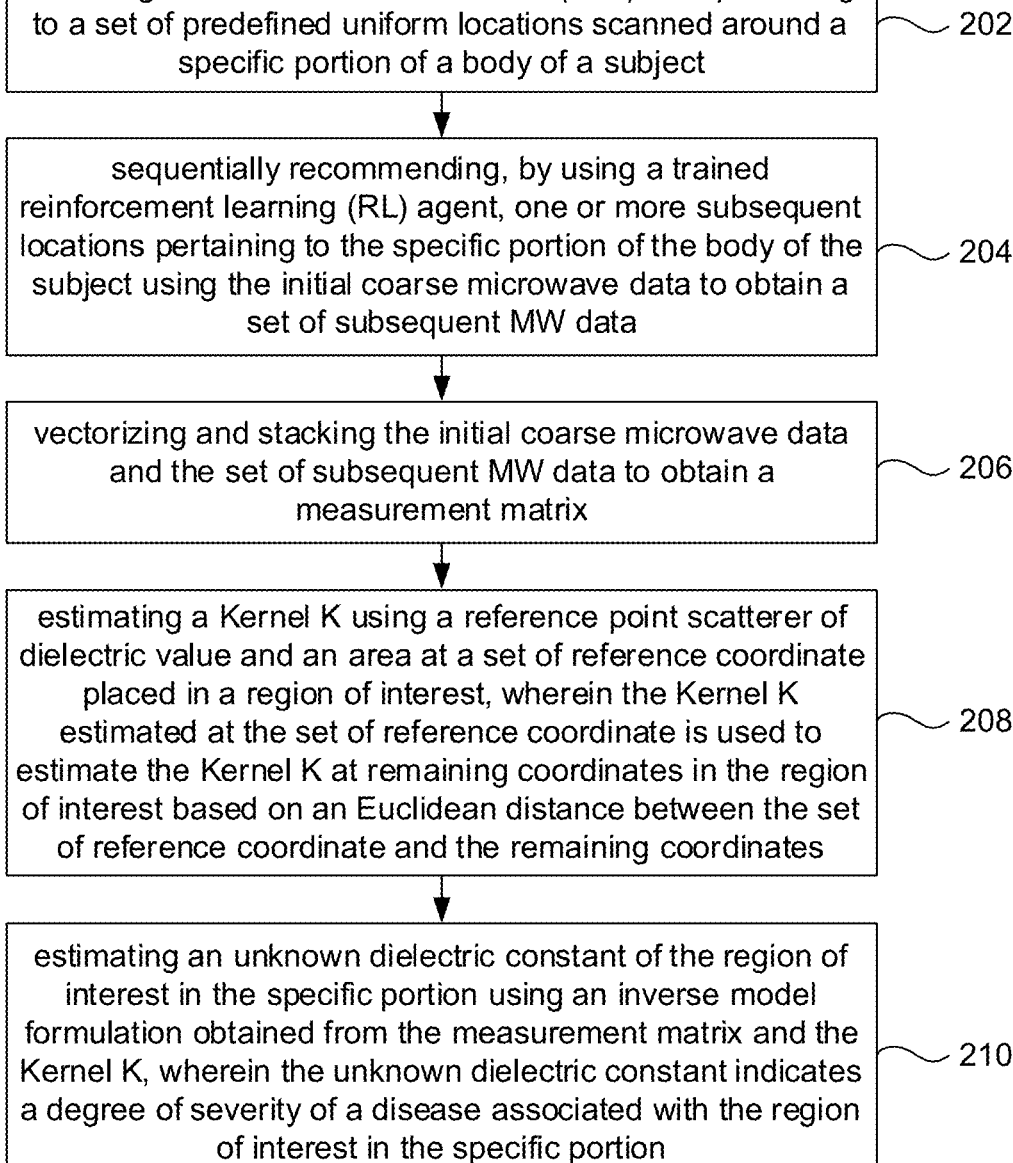

obtaining an initial coarse microwave (MW) data pertaining to a set of predefined uniform locations scanned around a specific portion of a body of a subject ⌐ 202 sequentially recommending, by using a trained reinforcement learning (RL) agent, one or more subsequent locations pertaining to the specific portion of the body of the subject using the initial coarse microwave data to obtain a set of subsequent MW data ⌐ 204 vectorizing and stacking the initial coarse microwave data and the set of subsequent MW data to obtain a measurement matrix ⌐ 206 estimating a Kernel K using a reference point scatterer of dielectric value and an area at a set of reference coordinate placed in a region of interest, wherein the Kernel K estimated at the set of reference coordinate is used to estimate the Kernel K at remaining coordinates in the region of interest based on an Euclidean distance between the set of reference coordinate and the remaining coordinates ⌐ 208 estimating an unknown dielectric constant of the region of interest in the specific portion using an inverse model formulation obtained from the measurement matrix and the Kernel K, wherein the unknown dielectric constant indicates a degree of severity of a disease associated with the region of interest in the specific portion ⌐ 210

FIG. 3

SYSTEMS AND METHODS FOR IN BODY MICROWAVE IMAGING OF A SUBJECT

PRIORITY CLAIM

This U.S. patent application claims priority under 35 U.S.C. § 119 to: Indian patent application No. 202321041564, filed on Jun. 19, 2023. The entire contents of the aforementioned application are incorporated herein by reference.

TECHNICAL FIELD

The disclosure herein generally relates to microwave imaging (MWI) techniques, and, more particularly, to systems and methods for in body microwave imaging of a subject.

BACKGROUND

Cancer (e.g., breast cancer) is one of the most prevalent diseases in the world (e.g., predominantly occurring in women). Detecting cancer early can significantly reduce the mortality rate, but this still remains a challenge owing to shortcomings in early screening and detection with existing modalities. Detection of cancer is typically done using screening methods such as X-ray mammography, Magnetic Resonance Imaging (MRI) and Ultrasound imaging (US), out of which X-ray mammography is considered as a standard detection method. But these conventional methods have their own limitations such as compression discomfort, inherent health risks, expensive, and consumes more time and effort.

SUMMARY

Embodiments of the present disclosure present technological improvements as solutions to one or more of the above-mentioned technical problems recognized by the inventors in conventional systems.

For example, in one aspect, there is provided a processor implemented method for an in-body microwave (MW) imaging of a subject. The method comprises obtaining, via one or more hardware processors, an initial coarse microwave (MW) data pertaining to a set of predefined uniform locations scanned around a specific portion of a body of a subject; sequentially recommending, by using a trained reinforcement learning (RL) agent, via the one or more hardware processors, one or more subsequent locations pertaining to the specific portion of the body of the subject using the initial coarse microwave data to obtain a set of subsequent MW data; vectorizing and stacking, via the one or more hardware processors, the initial coarse microwave data and the set of subsequent MW data to obtain a measurement matrix; estimating, via the one or more hardware processors, a Kernel K using a reference point scatterer of dielectric value $\varepsilon_0$ and an area $A_r$ at a set of reference coordinate placed in a region of interest, wherein the Kernel K estimated at the set of reference coordinate is used to estimate the Kernel K at remaining coordinates in the region of interest based on an Euclidean distance between the set of reference coordinate and the remaining coordinates; and estimating, via the one or more hardware processors, an unknown dielectric constant of the region of interest in the specific portion using an inverse model formulation obtained from the measurement matrix and the Kernel K, wherein the unknown dielectric constant indicates a degree of severity of a disease associated with the region of interest in the specific portion.

In an embodiment, the trained reinforcement learning (RL) agent is obtained by: defining a state set, an action set, an environment, and a reward pertaining to acquisition of MW data, wherein the state set is defined by a set of reconstructed microwave (MW) images that is used by the RL agent to select an action, wherein an initial state obtained from an initial coarse MW data enables the RL agent to select an optimal action from the action set, wherein the action set comprises a set of positions from which the set of subsequent MW data is acquired, wherein MW data pertaining to a specific action is collected based on a location being recommended, the environment reconstructs a next state of the region of interest based on the MW data collected from a set of cumulative actions selected by the RL agent, wherein a reward is computed by comparing a current state with a ground truth state obtained by using an entire MW data obtained from a plurality of possible acquisition positions, and wherein the current state, the action, the next state, and the reward constitutes a replay memory buffer data being stored in the replay memory buffer; randomly sampling data amongst the replay memory buffer data stored in a replay memory buffer to obtain sampled data; computing a mean square error (MSE) loss using the randomly sampled data based on a pre-defined equation; and training one or more network parameters of a Double Deep Q Network (DDQN), wherein the DDQN serves as the trained RL agent, wherein during the training, the MSE loss serves as feedback to the RL agent for a given-state-action pair; and deploying the trained RL agent in the environment for scanning to obtain one or more optimal action indices required for estimating the unknown dielectric constant.

In an embodiment, the step of training the one or more network parameters of the DDQN is preceded by: receiving a MW image; generating a value function for one or more action sets based on the MW image; and selecting at least one action from the one or more action sets based on an associated maximum value function.

In an embodiment, a dielectric constant (value) and an area of a first type of cells (normal cells) and a second type of cells (area of abnormal cells is sparse in nature) in the region of interest are different from each other.

In an embodiment, the unknown dielectric constant of the region of interest estimated uses a sparsity constraint which is based on the dielectric constant and the area.

In an embodiment, the unknown dielectric constant of the region of interest is estimated using an iterative threshold technique.

In an embodiment, number of MW data to be acquired for an episode is based on a scanning duration, and the scanning duration is one of a pre-determined duration or an empirically determined duration.

In an embodiment, the region of interest comprises a tissue.

In another aspect, there is provided a processor implemented system for in body microwave (MW) imaging of a subject. The system comprises: a memory storing instructions; one or more communication interfaces; and one or more hardware processors coupled to the memory via the one or more communication interfaces, wherein the one or more hardware processors are configured by the instructions to: obtain an initial coarse microwave (MW) data pertaining to a set of predefined uniform locations scanned around a specific portion of a body of a subject; sequentially recommend, by using a trained reinforcement learning (RL) agent, one or more subsequent locations pertaining to the specific portion of the body of the subject using the initial coarse microwave data to obtain a set of subsequent MW data; vectorize and stack the initial coarse microwave data and the set of subsequent MW data to obtain a measurement matrix; estimate a Kernel K using a reference point scatterer of dielectric value $\varepsilon_0$ and an area $A_r$ at a set of reference coordinate placed in a region of interest, wherein the Kernel K estimated at the set of reference coordinate is used to estimate the Kernel K at remaining coordinates in the region of interest based on an Euclidean distance between the set of reference coordinate and the remaining coordinates; and estimate an unknown dielectric constant of the region of interest in the specific portion using an inverse model formulation obtained from the measurement matrix and the Kernel K, wherein the unknown dielectric constant indicates a degree of severity of a disease associated with the region of interest in the specific portion.

In an embodiment, the trained reinforcement learning (RL) agent is obtained by: defining a state set, an action set, an environment, and a reward pertaining to acquisition of MW data, wherein the state set is defined by a set of reconstructed microwave (MW) images that is used by the RL agent to select an action, wherein an initial state obtained from an initial coarse MW data enables the RL agent to select an optimal action from the action set, wherein the action set comprises a set of positions from which the set of subsequent MW data is acquired, wherein MW data pertaining to a specific action is collected based on a location being recommended, the environment reconstructs a next state of the region of interest based on the MW data collected from a set of cumulative actions selected by the RL agent, wherein a reward is computed by comparing a current state with a ground truth state obtained by using an entire MW data obtained from a plurality of possible acquisition positions, and wherein the current state, the action, the next state, and the reward constitutes a replay memory buffer data being stored in the replay memory buffer; randomly sampling data amongst the replay memory buffer data stored in a replay memory buffer to obtain sampled data; computing a mean square error (MSE) loss using the randomly sampled data based on a pre-defined equation; and training one or more network parameters of a Double Deep Q Network (DDQN), wherein the DDQN serves as the trained RL agent, wherein during the training, the MSE loss serves as feedback to the RL agent for a given-state-action pair; and deploying the trained RL agent in the environment for scanning to obtain one or more optimal action indices required for estimating the unknown dielectric constant.

In an embodiment, prior to training the one or more network parameters of the DDQN, the one or more hardware processors are configured by the instructions to: receive a MW image; generate a value function for one or more action sets based on the MW image; and select at least one action from the one or more action sets based on an associated maximum value function.

In an embodiment, a dielectric constant (value) and an area of a first type of cells (normal cells) and a second type of cells (area of abnormal cells is sparse in nature) in the region of interest are different from each other.

In an embodiment, the unknown dielectric constant of the region of interest estimated uses a sparsity constraint which is based on the dielectric constant and the area.

In an embodiment, the unknown dielectric constant of the region of interest is estimated using an iterative threshold technique.

In an embodiment, number of MW data to be acquired for an episode is based on a scanning duration, and the scanning duration is one of a pre-determined duration or an empirically determined duration.

In an embodiment, the region of interest comprises a tissue.

In yet another aspect, there are provided one or more non-transitory machine-readable information storage mediums comprising one or more instructions which when executed by one or more hardware processors cause an in-body microwave (MW) imaging of a subject by obtaining an initial coarse microwave (MW) data pertaining to a set of predefined uniform locations scanned around a specific portion of a body of a subject; sequentially recommending, by using a trained reinforcement learning (RL) agent, one or more subsequent locations pertaining to the specific portion of the body of the subject using the initial coarse microwave data to obtain a set of subsequent MW data; vectorizing and stacking the initial coarse microwave data and the set of subsequent MW data to obtain a measurement matrix; estimating a Kernel K using a reference point scatterer of dielectric value $\varepsilon_0$ and an area $A_r$ at a set of reference coordinate placed in a region of interest, wherein the Kernel K estimated at the set of reference coordinate is used to estimate the Kernel K at remaining coordinates in the region of interest based on an Euclidean distance between the set of reference coordinate and the remaining coordinates; and estimating an unknown dielectric constant of the region of interest in the specific portion using an inverse model formulation obtained from the measurement matrix and the Kernel K, wherein the unknown dielectric constant indicates a degree of severity of a disease associated with the region of interest in the specific portion.

In an embodiment, the trained reinforcement learning (RL) agent is obtained by: defining a state set, an action set, an environment, and a reward pertaining to acquisition of MW data, wherein the state set is defined by a set of reconstructed microwave (MW) images that is used by the RL agent to select an action, wherein an initial state obtained from an initial coarse MW data enables the RL agent to select an optimal action from the action set, wherein the action set comprises a set of positions from which the set of subsequent MW data is acquired, wherein MW data pertaining to a specific action is collected based on a location being recommended, the environment reconstructs a next state of the region of interest based on the MW data collected from a set of cumulative actions selected by the RL agent, wherein a reward is computed by comparing a current state with a ground truth state obtained by using an entire MW data obtained from a plurality of possible acquisition positions, and wherein the current state, the action, the next state, and the reward constitutes a replay memory buffer data being stored in the replay memory buffer; randomly sampling data amongst the replay memory buffer data stored in a replay memory buffer to obtain sampled data; computing a mean square error (MSE) loss using the randomly sampled data based on a pre-defined equation; and training one or more network parameters of a Double Deep Q Network (DDQN), wherein the DDQN serves as the trained RL agent, wherein during the training, the MSE loss serves as feedback to the RL agent for a given-state-action pair; and deploying the trained RL agent in the environment for scanning to obtain one or more optimal action indices required for estimating the unknown dielectric constant.

In an embodiment, the step of training the one or more network parameters of the DDQN is preceded by: receiving a MW image; generating a value function for one or more action sets based on the MW image; and selecting at least one action from the one or more action sets based on an associated maximum value function.

In an embodiment, a dielectric constant (value) and an area of a first type of cells (normal cells) and a second type of cells (area of abnormal cells is sparse in nature) in the region of interest are different from each other.

In an embodiment, the unknown dielectric constant of the region of interest estimated uses a sparsity constraint which is based on the dielectric constant and the area.

In an embodiment, the unknown dielectric constant of the region of interest is estimated using an iterative threshold technique.

In an embodiment, number of MW data to be acquired for an episode is based on a scanning duration, and the scanning duration is one of a pre-determined duration or an empirically determined duration.

In an embodiment, the region of interest comprises a tissue.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 3 depicts an exemplary flow chart illustrating a method for an in-body microwave (MW) imaging of a subject, using the system of FIG. 1, in accordance with an embodiment of the present disclosure.

DETAILED DESCRIPTION

Figure 1:
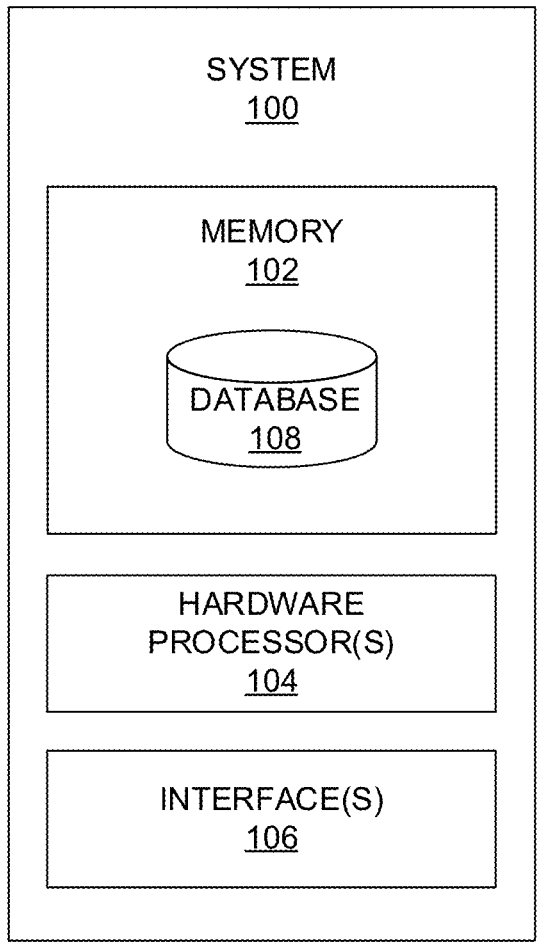
FIG. 1 depicts an exemplary system for an in-body microwave (MW) imaging of a subject, in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Cancer (e.g., breast cancer) is one of the most prevalent diseases in the world (e.g., predominantly occurring in women). Detecting breast cancer early can significantly reduce the mortality rate, but this still remains a challenge owing to shortcomings in early screening and detection with existing modalities. Detection of breast cancer is typically done using screening methods such as X-ray mammography, Magnetic Resonance Imaging (MRI) and Ultrasound imaging (US), out of which X-ray mammography is considered as a standard detection method. But these conventional methods have their own limitations such as compression discomfort, inherent health risks, expensive, and consumes more time and effort (e.g., refer "N. AlSawaftah, S. El-Abed, S. Dhou, and A. Zakaria, "Microwave imaging for early breast cancer detection: Current state, challenges, and future directions," Journal of Imaging, vol. 8, no. 5, p. 123, 2022."). Recently, Microwave Imaging (MWI) based techniques which can overcome some of the above-mentioned limitations have been explored in literature (e.g., refer N. AlSawaftah et. al).

MWI relies on the change in electrical properties when excited with electromagnetic waves. It has been observed that tumor cells have more water content as compared to normal cells and hence have higher dielectric properties of around 8-10% more than the normal cells (e.g., refer "T. Sugitani, S.-i. Kubota, S.-i. Kuroki, K. Sogo, K. Arihiro, M. Okada, T. Kadoya, M. Hide, M. Oda, and T. Kikkawa, "Complex permittivities of breast tumor tissues obtained from cancer surgeries," Applied Physics Letters, vol. 104, no. 25, p. 253702, 2014."). MWI is based on the principle of radar that excites electromagnetic waves and reflections from the breast are captured at different predefined locations. Further, these collected measurements are processed using various algorithms to reconstruct the MWI of the breast. Another literature (e.g., refer "X. Li and S. Hagness, "A confocal microwave imaging algorithm for breast cancer detection," IEEE Microwave and Wireless Components Letters, vol. 11, no. 3, pp. 130-132, 2001.") used Delay-And-Sum (DAS) which makes use of shifted time delay at different antenna positions. This is a fast and effective technique to reconstruct the image but results in significant clutter artifacts (e.g., refer "N. AlSawaftah, S. El-Abed, S. Dhou, and A. Zakaria, "Microwave imaging for early breast cancer detection: Current state, challenges, and future directions," Journal of Imaging, vol. 8, no. 5, p. 123, 2022"). Therefore, various improvements have been made on DAS resulting in different variants like Delay-Multiply-And-Sum (DMAS) (e.g., refer "H. B. Lim, N. T. T. Nhung, E.-P. Li, and N. D. Thang, "Confocal microwave imaging for breast cancer detection: Delay-multiply-and sum image reconstruction algorithm," IEEE Transactions on Biomedical Engineering, vol. 55, no. 6, pp. 1697-1704, 2008"), Improved Delay-And-Sum (IDAS) (e.g., refer "M. Klemm, I. Craddock, J. Leendertz, A. Preece, and R. Benjamin, "Improved delay-and-sum beamforming algorithm for breast cancer detection," International Journal of Antennas and Propagation, vol. 2008, 2008."), etc. An evaluation of these algorithms on clinical patients can be found in yet another conventional literature (e.g., refer "M. A. Elahi, D.

O'Loughlin, B. R. Lavoie, M. Glavin, E. Jones, E. C. Fear, and M. O'Halloran, "Evaluation of image reconstruction algorithms for confocal microwave imaging: Application to patient data," Sensors, vol. 18, no. 6, p. 1678, 2018."), where only DAS and DMAS were consistent with clinical reports, with DMAS having significantly reduced clutter. Further, these techniques require dense radar measurements to obtain a good quality MWI (e.g., refer Li et. al, Lim et. al, Klemm et. al, "M. A. Elahi, D. O'Loughlin, B. R. Lavoie, M. Glavin, E. Jones, E. C. Fear, and M. O'Halloran, "Evaluation of image reconstruction algorithms for confocal microwave imaging: Application to patient data," Sensors, vol. 18, no. 6, p. 1678, 2018. ", "N. K. Nikolova, Introduction to microwave imaging. Cambridge University Press, 2017.", and "D. Tajik, F. Foroutan, D. S. Shumakov, A. D. Pitcher, and N. K. Nikolova, "Real-time microwave imaging of a compressed breast phantom with planar scanning," IEEE Journal of Electromagnetics, RF and Microwaves in Medicine and Biology, vol. 2, no. 3, pp. 154-162, 2018.). This makes the entire system more time-consuming and hence is not preferrable in the present case. On the other hand, more recently, N. K. Nikolova and Tijak et. al proposed Quantitative Microwave Imaging (QMI) techniques by employing the point spread function (PSF). Direct inversion techniques such as in N. K. Nikolova is typically used to solve QMI technique but this is computationally more complex and also error prone. Further, to reduce computational complexity, Tijak et. al described 2D FFT based technique, but this requires a 2D grid-based scanning with very dense radar measurements. While QMI based approach looks promising, the above limitations have to be efficiently addressed to make it deployment friendly.

Embodiments of the present disclosure provide systems that implement a microwave imaging-based tumor detection approach referred to as "Enhanced Microwave imaging for efficient breast Tumor Detection" or method of the present disclosure. The method of the present disclosure addresses the aforementioned MWI limitations by using a computationally efficient model-based reconstruction algorithm and an intelligent radar scanning mechanism to reduce the scan duration. Firstly, the system of the present disclosure formulates the model-based MWI (herein referred as method of the present disclosure) as an inverse image reconstruction problem by building the forward model using the PSF (which may be obtained via calibration). Since the tumor content is sparse and localized to fewer regions, the system of the present disclosure solves the inverse problem efficiently by using sparsity as a prior. Next, to reduce the number of scanning measurements, an intelligent scanning mechanism based on Deep Reinforcement Learning (DRL) approach is implemented to optimize the radar acquisition locations. The number of measurements (say based on maximum duration) or scans in a given episode of tumor detection is fixed and a coarse uniform scan is firstly performed to obtain an initial MWI. This coarse level image helps the RL agent to optimally suggest the remaining acquisition points. The method of the present disclosure has been benchmarked against the existing/conventional methods using an open dataset collected using 3D breast phantoms having tumor. Both the visual results and Signal to Mean Ratio (SMR) is provided to compare the performance of the method of the present disclosure with the other standard/conventional DAS and DMAS approaches. The results clearly show that the method of the present disclosure provides improved tumor localized image with reduced clutter and shows up to 2 times SMR improvement over other existing techniques. Further, only a marginal visual deterioration is observed with the method of the present disclosure despite using only 33% of the total measurements.

Referring now to the drawings, and more particularly to FIGS. 1 through 8, where similar reference characters denote corresponding features consistently throughout the figures, there are shown preferred embodiments and these embodiments are described in the context of the following exemplary system and/or method.

FIG. 1 depicts an exemplary system 100 for an in-body microwave (MW) imaging of a subject, in accordance with an embodiment of the present disclosure. The system 100 may also be referred as 'an in-body imaging system', 'an imaging system', or 'an unknown dielectric constant estimation system', and may be interchangeably used herein. In an embodiment, the system 100 includes one or more hardware processors 104, communication interface device (s) or input/output (I/O) interface(s) 106 (also referred as interface(s)), and one or more data storage devices or memory 102 operatively coupled to the one or more hardware processors 104. The one or more processors 104 may be one or more software processing components and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor (s) is/are configured to fetch and execute computer-readable instructions stored in the memory. In an embodiment, the system 100 can be implemented in a variety of computing systems, such as laptop computers, notebooks, hand-held devices (e.g., smartphones, tablet phones, mobile communication devices, and the like), workstations, mainframe computers, servers, a network cloud, and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random-access memory (SRAM) and dynamic-random access memory (DRAM), and/or non-volatile memory, such as read only memory (ROM), erasable programmable ROM, flash memories, hard disks, optical disks, and magnetic tapes. In an embodiment, a database 108 is comprised in the memory 102, wherein the database 108 comprises information pertaining to coarse microwave (MW) data pertaining to a set of predefined uniform locations scanned around a specific portion (e.g., breast) of a body of a subject, one or more subsequent locations pertaining to the specific portion of the body of the subject using the initial coarse microwave data, measurement matrix, Kernel K, unknown dielectric constant, and the like. The database 108 further comprises one or more Double Deep Q Networks which when trained serve as one or more trained reinforcement learning (RL) agent, and the like. The memory 102 further comprises (or may further comprise) information pertaining to input(s)/output(s) of each step performed by the systems and methods of the present disclosure. In other words, input(s) fed at each step and output(s) generated at each step are comprised in the memory 102 and can be utilized in further processing and analysis.

Figures 2A, 2B:
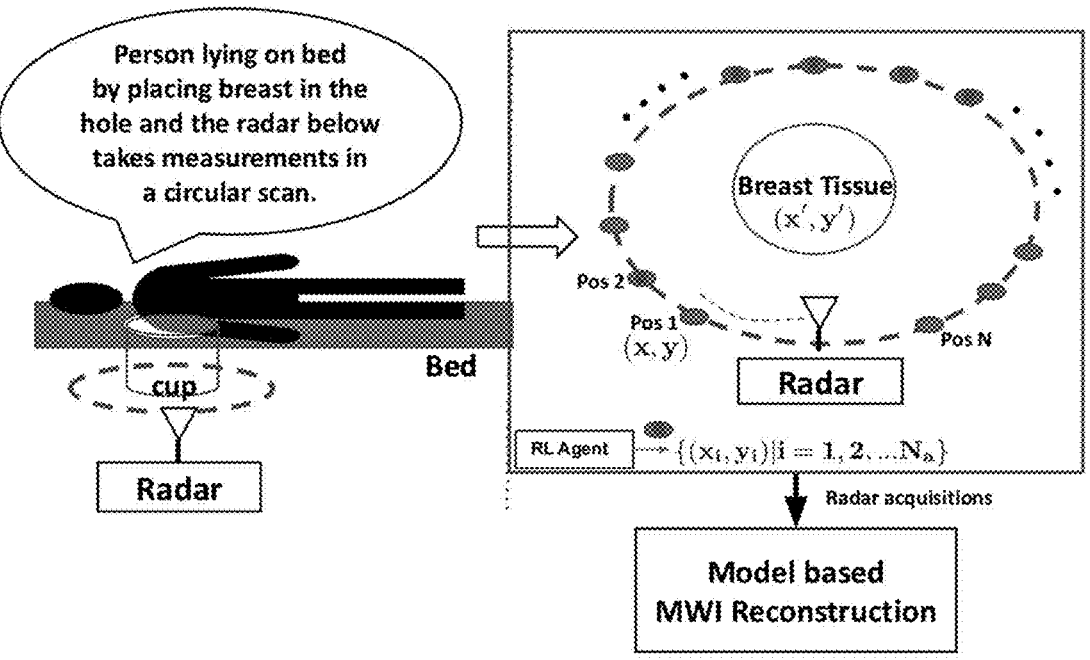
FIGS. 2A and 2B depict (a) an illustration of a subject undergoing detection test, and (b) a detailed view demonstrating the $N_a$ optimized locations selected by the RL agent from a total of N possible radar locations around the breast tissue, in accordance with an embodiment of the present disclosure.

FIGS. 2A and 2B, with reference to FIG. 1, depict (a) an illustration of a subject undergoing detection test, and (b) a detailed view demonstrating the $N_a$ optimized locations selected by the RL agent from a total of N possible radar locations around the breast tissue, in accordance with an embodiment of the present disclosure. More specifically, FIG. 2A illustrates the typical deployment the method, where the subject simply lie on the bed by placing the breast inside a cup. The radar which is placed below takes measurements at different antenna positions in a circular manner. The simplified view of radar scan is shown in FIG. 2B, where the radar measurements taken at different locations are fed to a model-based MWI reconstruction algorithm to detect tumors. The RL agent intelligently chooses $N_a$ locations from N ($N_a<N$) total measurements so that the overall scan duration is reduced, without compromising on the MWI image quality.

FIG. 3 depicts an exemplary flow chart illustrating a method for an in-body microwave (MW) imaging of a subject, using the system 100 of FIG. 1, in accordance with an embodiment of the present disclosure. In an embodiment, the system(s) 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to components of the system 100 of FIG. 1, the illustrations of FIGS. 2A and 2B, and the flow diagram as depicted in FIG. 3. Further, although process steps, method steps, techniques or the like may be described in a sequential order, such processes, methods, and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

At step 202 of the method of the present disclosure, the one or more hardware processors 102 obtain an initial coarse microwave (MW) data pertaining to a set of predefined uniform locations scanned around a specific portion (e.g., breast) of a body of a subject. The scanning is performed by employed a scanning radar, in one example embodiment.

At step 204 of the method of the present disclosure, the one or more hardware processors 102 sequentially recommending, by using a trained reinforcement learning (RL) agent, one or more subsequent locations pertaining to the specific portion of the body of the subject using the initial coarse microwave (MW) data to obtain a set of subsequent MW data. The number of MW data to be acquired for an episode is based on a scanning duration and the scanning duration is one of a pre-determined duration or an empirically determined duration. The system 100 prefixes the number of measurements (e.g., say based on maximum duration) in a given episode of tumor detection and an initial coarse uniform scan is firstly performed to obtain an initial MWI. This coarse level image helps the RL agent to optimally suggest the remaining acquisition points (refer steps 202 and 204). The step of training the RL agent is better understood by way of following description:

The radar acquisition setup is based on a Deep Reinforcement Learning (DRL) framework, where the task is to find optimized radar locations (e.g., the set of predefined uniform locations), (x, y), to ensure quick and accurate tumor detection. The DRL system has the following components (e.g., refer "L. Pineda, S. Basu, A. Romero, R. Calandra, and M. Drozdzal, "Active mr k-space sampling with reinforcement learning," in Medical Image Computing and Computer Assisted Intervention-MICCAI 2020: $23^{rd}$ International Conference, Lima, Peru, Oct. 4-8, 2020, Proceedings, Part II 23. Springer, 2020, pp. 23-33."): (1) A set of states that defines observations received from the environment (2) policy denoted by π that enables to decide an action based on any given state, (3) an environment that responds to the action taken by the agent to output the next state, and (4) a reward for a given state action pair to indicate its performance.

Figure 4:
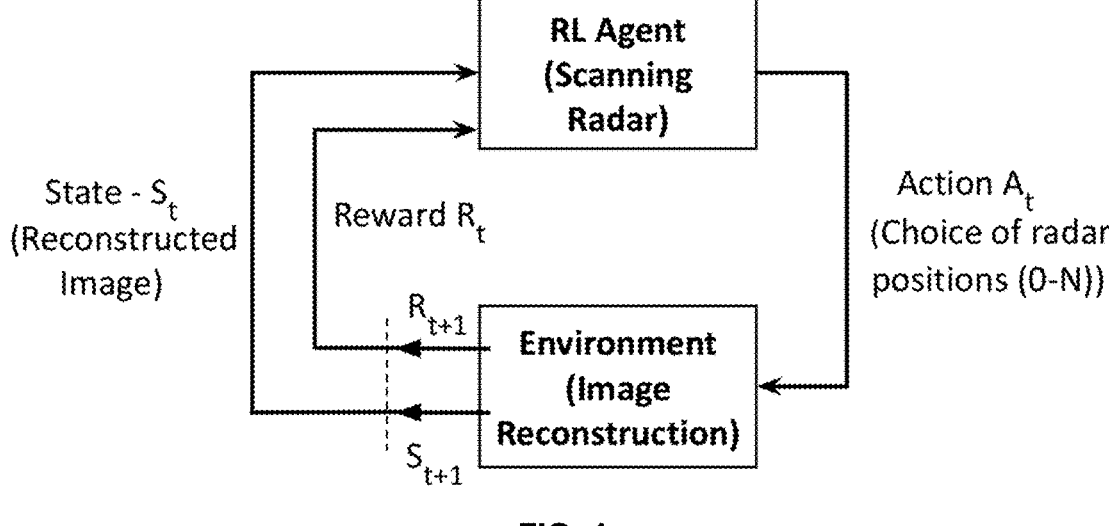
FIG. 4 depicts a block diagram of a deep reinforcement learning (DRL or RL agent) comprised in the system of FIG. 1, in accordance with an embodiment of the present disclosure.

DRL formulation: The DRL building blocks with respect to the system 100 at any given time t is shown in FIG. 4. More specifically, FIG. 4, with reference to FIGS. 1 through 3, depicts a block diagram of the deep reinforcement learning comprised in the system 100 of FIG. 1, in accordance with an embodiment of the present disclosure.

Agent: The scanning radar acts like an RL agent.

State set: A set of reconstructed microwave image $S_t$ reconstructed by the environment that is used by the agent to choose an action.

Action set: The set of all positions from which the radar can acquire measurements, i.e., $A_t \in \{1, 2, \ldots, N\}$. Note that for a given episode an already observed action are removed from the action space as taking measurements from same location does not help in improving the image reconstruction.

Environment: Based on the cumulative actions selected by the agent, a microwave image of scene is reconstructed. In the implementation of the system and method, the system 100 used DAS algorithm (e.g., refer "X. Li and S. Hagness, "A confocal microwave imaging algorithm for breast cancer detection," IEEE Microwave and Wireless Components Letters, vol. 11, no. 3, pp. 130-132, 2001.") for generating the next state image. The DAS is chosen as it is fast, but it is important to note that one can employ any other algorithm like the one described herein. This image is then fed as the next state to the RL agent for further acquisitions.

Reward function (also referred as 'reward' and interchangeably used herein): For training the agent, the system 100 used the following reward function $R=1-MSE(S_t, GT)$, where MSE denotes the Mean Square Error between the state image $S_t$ and ground truth image GT obtained using all measurements.

Discount factor: a hyper parameter γ that indicates the importance given to future rewards.

The above formulation is better understood by definitions are better understood by way of following description:

A state set, an action set, an environment, and a reward pertaining to acquisition of MW data are defined. The state set is defined by a set of reconstructed microwave (MW) images that is used by the RL agent to select an action. An initial state obtained from an initial coarse MW data enables the RL agent to select an optimal action from the action set. The action set comprises a set of positions from which the set of subsequent MW data is acquired. The MW data pertaining to a specific action is collected based on a location being recommended. The environment reconstructs a next state of the region of interest based on the MW data collected from a set of cumulative actions selected by the RL agent. The reward is computed by comparing a current state with a ground truth state obtained by using an entire MW data obtained from a plurality of possible acquisition positions. Further, the current state, the action, the next state, and the reward constitutes the replay memory buffer data being stored in the replay memory buffer. The step of defining the RL agent is better understood by way of following description:

In a given episode of tumor detection, the system 100 and the method restrict the number of radar acquisitions, $N_a<N$ based on the maximum scanning time. Initially, a coarse level scan having $N_u$, $N_u<N_a$ measurements is taken at uniform distances to obtain a coarse MWI $S_0$. This initial state $S_0$ helps the RL agent about the approximate tumor location and further select an optimal action from the action space At. The scanning radar then moves to that suggested location and collects data corresponding to that action. This data is then used by the DAS algorithm (environment) to reconstruct the next MWI state $S_t+1$. A reward is also computed by comparing the current state $S_t$ with the ground truth DAS image GT obtained by using all the measurements and this is fed back to the RL agent to give feedback for a given state-action pair (only during training). The RL agent then uses $S_t+1$ to choose the next action in the given episode. These steps are repeated until the given episode is completed. The RL agent must suitably be trained to choose the optimal radar positions for a given MWI state.

Figure 5:
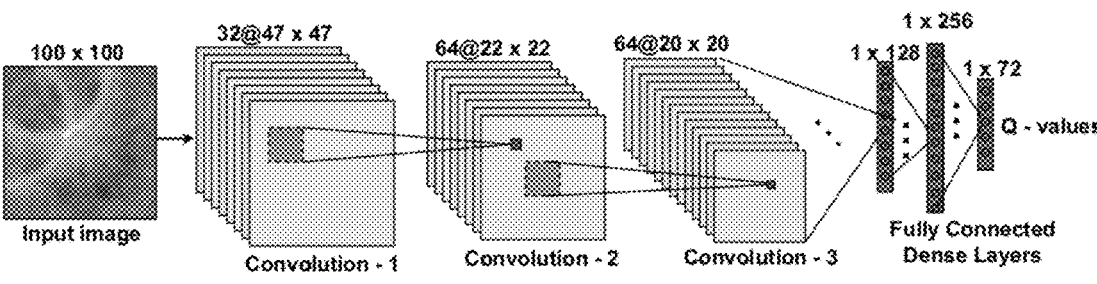
FIG. 5 depicts a Double Deep Q Network (DDQN) value architecture for training a reinforcement learning (RL) agent, in accordance with an embodiment of the present disclosure.

Once the above parameters are defined, a MW image, a value function for one or more action sets is generated based on the MW image, and at least one action from the one or more action sets is selected based on an associated maximum value function. Further, data amongst the replay memory buffer data stored in a replay memory buffer is randomly sampled to obtain sampled data. A mean square error (MSE) loss is then computed using the randomly sampled data based on a pre-defined equation (e.g., Bellman equation(s)). One or more network parameters of a Double Deep Q Network (DDQN) are then trained, wherein DDQN serves as the trained RL agent. During the training, the MSE loss serves as feedback to the RL agent for a given-state-action pair. Once the trained RL agent is obtained, the trained RL agent is then deployed in the environment for scanning to obtain one or more optimal action indices required for estimating the unknown dielectric constant. The above step of training the RL agent and deployment is better understood by way of following description:

The RL agent tries to learn a policy $\pi(S_t; \theta) \to A_t$ At that enables it to select an action $A_t$ given a MWI state $S_t$. This policy can be learnt using state-of-the-art DRL techniques (e.g., refer "M. Hessel, J. Modayil, H. Van Hasselt, T. Schaul, G. Ostrovski, W. Dabney, D. Horgan, B. Piot, M. Azar, and D. Silver, "Rainbow: Combining improvements in deep reinforcement learning," in Proceedings of the AAAI conference on artificial intelligence, vol. 32, no. 1, 2018.", and "H. Van Hasselt, A. Guez, and D. Silver, "Deep reinforcement learning with double q-learning," in Proceedings of the AAAI conference on artificial intelligence, vol. 30, no. 1, 2016."). In the present disclosure, the system and method described herein used a Double Deep Q Networks (DDQN) (e.g., refer H. Van Hasselt et al.) to train the RL agent. The value network architecture similar to state-of-the-art (e.g., L. Pineda, S. Basu, A. Romero, R. Calandra, and M. Drozdzal, "Active mr k-space sampling with reinforcement learning," in Medical Image Computing and Computer Assisted Intervention-MICCAI 2020: $23^{rd}$ international Conference, Lima, Peru, Oct. 4-8, 2020, Proceedings, Part II 23. Springer, 2020, pp. 23-33.) employed in the DDQN is shown in FIG. 5, which consists of three convolutional layers followed by a fully connected dense layers. More specifically, FIG. 5, with reference to FIGS. 1 through 4, depicts a Double Deep Q Network (DDQN) value architecture for training the RL agent, in accordance with an embodiment of the present disclosure. The MWI image is fed as input to the DDQN and the DDQN outputs the value function corresponding to all the possible action space N. Further the policy can be obtained by greedily selecting an action based on this value function. An optimum $\pi(S_t; \theta)$ can be obtained by suitably training the network parameters $\theta$. For training, the system 100 first randomly samples data from the replay memory buffer that consist of data tuple consisting of information about the state, action taken, reward obtained, and the next state. This sampled data from replay buffer is used to compute the loss based on the bellman equations and this is propagated to train the DDQN network parameters $\theta$. A modified epsilon greedy exploration policy has been used to fill the replay buffer (e.g., refer "R. S. Sutton and A. G. Barto, Reinforcement learning: An introduction. MIT press, 2018."). For further details on training refer to (e.g., "H. Van Hasselt, A. Guez, and D. Silver, "Deep reinforcement learning with double q-learning," in Proceedings of the AAAI conference on artificial intelligence, vol. 30, no. 1, 2016."). The trained network can then be deployed for intelligent scanning which gives the optimal action indices required for the model-based MWI reconstruction. For instance, based on the maximum scanning time, the system 100 prefixes the maximum number of acquisitions $N_a$ for an episode. $N_u$ scans are taken at uniform locations to obtain the initial coarse microwave image. The trained RL agent then uses this coarse image to sequentially suggest the remaining $(N_a-N_u)$ locations. The radar (or MW) data at these acquired locations is then fed to the model-based MWI reconstruction for improving MWI.

Referring to steps of FIG. 3, at step 206 of the method of the present disclosure, the one or more hardware processors 102 vectorize and stack the initial coarse microwave data and the set of subsequent MW data to obtain a measurement matrix. At step 208 of the method of the present disclosure, the one or more hardware processors 102 estimate a Kernel K using a reference point scatterer of dielectric value $\varepsilon_0$ and an area $A_r$ at a set of reference coordinate placed in a region of interest. The Kernel K estimated at the set of reference coordinate is used to estimate the Kernel K at remaining coordinates in the region of interest based on an Euclidean distance between the set of reference coordinate and the remaining coordinates. Further, at step 210 of the method of the present disclosure, the one or more hardware processors 102 estimate an unknown dielectric constant of the region of interest in the specific portion using an inverse model formulation obtained from the measurement matrix and the Kernel K. The unknown dielectric constant indicates a degree of severity (e.g., stage 1, stage 2, stage 'n', and so on) of a disease (e.g., breast cancer) associated with the region of interest in the specific portion. Dielectric constant (value) and an area of a first type of cells (e.g., normal cells) and a second type of cells (area of abnormal cells is sparse in nature) in the region of interest are different from each other. More specifically, area of the abnormal cells (e.g., the second type of cells is sparse in nature). Due to this sparsity nature of the area, the unknown dielectric constant of the region of interest is estimated using a sparsity constraint. Thus, the sparsity constraint is based on the dielectric constant and the area, and the unknown dielectric constant of the region of interest is estimated using an iterative threshold technique.

The above steps of 206 through 210 are better understood by way of following description:

A monostatic radar time domain model of microwave scattering denoted by m(x, y, t) captured at antenna position (x, y) and at time t can be expressed as:

$$m(x, y, t) = \int \int_{x',y'} \varepsilon(x', y') \underbrace{\left[ h_{rx}^{inc} * \frac{\partial^2 E_{tx}^{inc}}{\partial t^2} \right]}_{Kernel=K(x,y,x',y',t)} dx'dy' \qquad (1)$$

where $\varepsilon(x', y')$ denotes the unknown dielectric constant of the breast tissue to be estimated at location (x', y'), $$h_{rx}^{inc}$$

denotes the impulse field response and $$E_{tx}^{inc}$$

denotes the total electric field by transmitter antenna (e.g., refer (e.g., "N. K. Nikolova, Introduction to microwave imaging. Cambridge University Press, 2017.") for further details). It is to be noted from equation (1) that to compute unknown & in equation (1), the system 100 and the method described herein require the knowledge of the Kernel K. K depends upon the system 100 and the system 100 used the following approach to determine it.

Estimation of Kernel K: The system 100 and the method described herein use calibration measurement to estimate K. The system 100 and the method further assume a reference point scatterer of dielectric value $\varepsilon_0$ and area $A_r$ at position $$(x'_r, y'_r),$$

then K from (1) can be approximated:

$$K(x, y, x'_r, y'_r, t) \simeq \frac{m(x, y, t)}{\varepsilon_0 A_r} \qquad (2)$$

This reference measurement corresponding to a point scatterer can be obtained either through simulations or by experiments. Although simulation enables the system 100 and the method to precisely define the dielectric and environment properties, in practice using a calibration measurement from actual experimental data is found to be more effective. Since, the system 100 and the method described herein used an open dataset (e.g., "T. Reimer, J. Krenkevich, and S. Pistorius, "An open-access experimental dataset for breast microwave imaging," in 2020 14th European Conference on Antennas and Propagation (EuCAP). IEEE, 2020, pp. 1-5.") for validation, the system 100 and the method of the present disclosure have used the time domain output pulse obtained from the VNA provided along with the dataset (e.g., refer T. Reimer et. al as mentioned above) for estimating K. The system 100 and the method described herein further assumes that the background is uniform, and uses the Kernel K $$(x, y, x'_r, y'_r, t)$$

of the reference measurement to estimate the Kernel at any point (x', y') using the following:

$$K(x, y, x'_r, y'_r, t) \simeq K(x, y, x'_r, y'_r, t - \partial t(x', y')) \qquad (3)$$

where $$\partial t(x', y') = \frac{\delta d}{c},$$

where $\delta d$ is defined as the Euclidean distance between where the reference measurement $$(x'_r, y'_r)$$

and point of interest (x', y'). It is important to observe that the kernel function K depends only on the system 100 and is independent of $\varepsilon$. Thus, it needs to be evaluated only once for a given experimental setup.

Reconstruction: Discretizing the entire imaging plane into $N_x \times N_y$ and using (3), equation (1) can be expressed as follows:

$$m(x, y, t) \simeq \Sigma_{x'} \Sigma_{y'} \varepsilon(x', y') \ K(x, y, x'_r, y'_r, t - \partial t(x', y')) \qquad (4)$$

By stacking all the measurements after vectorization, the following inverse model formulation is obtained:

$$m = K\varepsilon + \eta \qquad (5)$$

where $m \in \mathbb{C}^{N_a N_t \times 1}$, $K \in \mathbb{C}^{N_a N_t \times N_x N_y}$, $\varepsilon \in \mathbb{C}^{N_x N_y \times 1}$ and $N_t$ denotes the number of time instances taken at a particular antenna location (x, y). The dielectric constant of the tumor is large (e.g., the second type of cells) as compared to other cells (e.g., first type of cells) (e.g., refer "T. Sugitani, S.-i. Kubota, S.-i. Kuroki, K. Sogo, K. Arihiro, M. Okada, T. Kadoya, M. Hide, M. Oda, and T. Kikkawa, "Complex permittivities of breast tumor tissues obtained from cancer surgeries," Applied Physics Letters, vol. 104, no. 25, p. 253702, 2014."). In other words, only a few pixels of the reconstructed image & corresponding to tumor will be significant whereas the other regions corresponding to normal cells can be neglected. Hence, the system 100 can assume (or assumes) $\varepsilon$ to be sparse and equation (5) can be written as:

$$\varepsilon = \arg \min_{\varepsilon} \|m - K\varepsilon\|_2^2 + \lambda \|\varepsilon\|_1 \qquad (6)$$

where the $\ell_1$ regularizer $\|\varepsilon\|_1$ is introduced as it is well known to introduce sparse solutions and $\lambda$ is a hyper parameter which controls the amount of regularization. The reconstructed MW image $\varepsilon$ is obtained using soft thresholding and can be solved using ISTA algorithm (A Fast Iterative Shrinkage-Thresholding Algorithm), whose $(k+1)^{th}$ iterative update is shown below:

$$\varepsilon^{(k+1)} = \mathrm{soft}\left(\varepsilon^k + \frac{1}{\alpha}K^T\left(m - K\varepsilon^{(k)}\right), \frac{\lambda}{2\alpha}\right) \quad (7)$$

where $\alpha$ indicates the learning rate. On implementation, it was observed that for most instances, the above solution was converging with less than k=5 iterations. However, for efficient implementation an unfolded variant of equation (7) can also be used to make it faster.

It is to be noted that the inverse modeling approach of the system 100 and the method of the present disclosure performs significantly better than conventional standard DAS and DMAS approaches. It is to be further observed that taking more measurements of m(x, y, t) not only increases the dimension of equation (6) (leading to increase in computational complexity), but as described earlier it is also not preferable in practice as it leads to increase in total scan duration. Thus, the scanning approach described above based on the DRL framework is implemented to reduce this scan duration.

Results:

In order to validate the system 100 and the method of the present disclosure, an openly available dataset as mentioned above has been used.

Dataset (refer "T Reimer et. al"): The open dataset contained three-dimensional (3D) Magnetic resonance imaging (MRI) derived breast phantoms from 9 patients having breast cancer. The phantoms were made using different tissue layers such as adipose shell, fibro glandular shell and was filled with liquids to mimic the breast composition. Tumor dielectric properties were modeled using spherical glass tubes that were immersed into these phantoms. The entire breast phantoms composition along with the tumor were placed in the center and the radar collects data at N=72 antenna positions in a circular motion. The microwave dataset comprised of different permutation of adipose shells (A1-A3), fibroglandular shells (F1-F5) and different size of tumor ranging from (1 cm-3 cm) in radius. The ground truth size and location of tumor were given in the dataset to compare the MWI reconstruction performance. The RL training was done on a set of 120 instances from this dataset each containing 72 radar measurements and the performance of the trained RL agent has been evaluated for 20 test instances. Model-based MWI reconstruction:

The system 100 compares the performance of the model-based MWI reconstruction (e.g., method of the present disclosure) against the standard DAS (e.g., refer "X. Li and S. Hagness, "A confocal microwave imaging algorithm for breast cancer detection," IEEE Microwave and Wireless Components Letters, vol. 11, no. 3, pp. 130-132, 2001."), DMAS (e.g., refer "H. B. Lim, N. T. T. Nhung, E.-P. Li, and N. D. Thang, "Confocal microwave imaging for breast cancer detection: Delay-multiply-and sum image reconstruction algorithm," IEEE Transactions on Biomedical Engineering, vol. 55, no. 6, pp. 1697-1704, 2008."). It is to be observed that, for this comparison the intelligent scanning has not been considered, and all N=72 measurements were used. The 2-D Fast Fourier Transformation (FFT) based Quantitative Medical Imaging (QMI) approach mentioned in conventional literature (e.g., refer "D. Tajik, F. Foroutan, D. S. Shumakov, A. D. Pitcher, and N. K. Nikolova, "Real-time microwave imaging of a compressed breast phantom with planar scanning," IEEE Journal of Electromagnetics, RF and Microwaves in Medicine and Biology, vol. 2, no. 3, pp. 154-162, 2018.") required a very dense 2D scanning system for MWI which was not available with this dataset and hence this result has not been provided. Since the dataset did not provide any calibration data, the system 100 and the method of the present disclosure approximated the Kernel K by using the time domain output pulse from the VNA (e.g., refer "T. Reimer et. al mentioned above"). The value of a and/after tuning was set to 0.1 and 50 respectively for the optimization framework.

Figure 6:
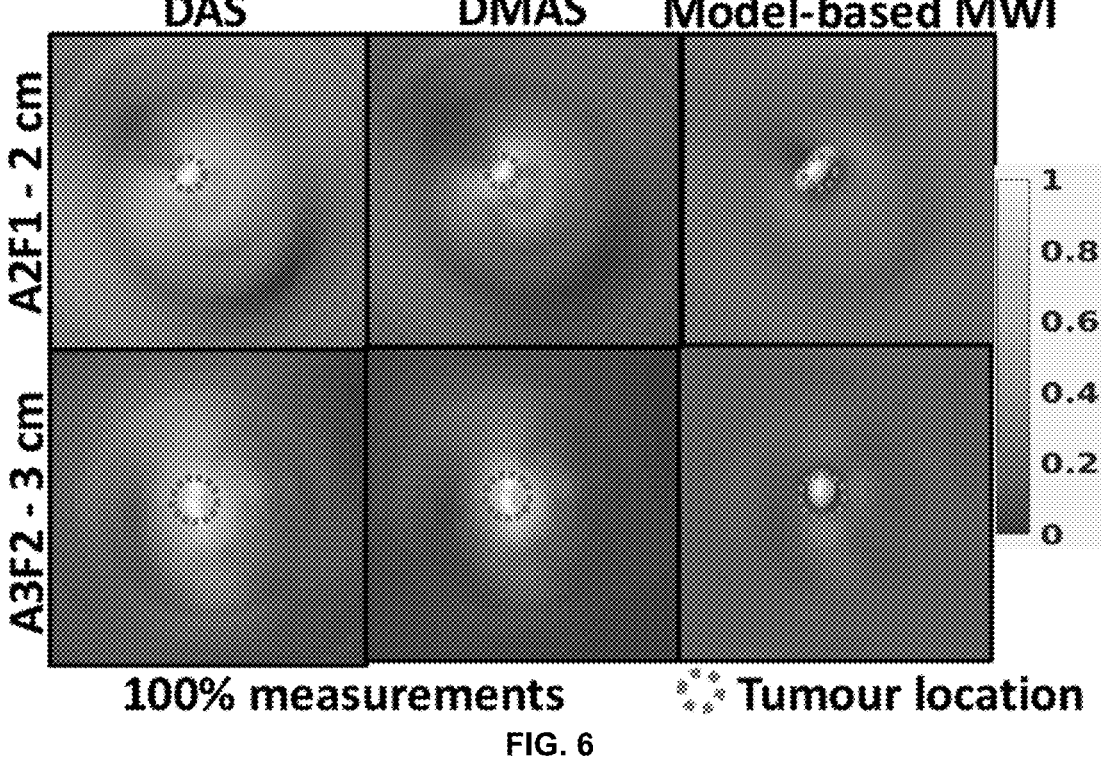
FIG. 6 shows a reconstructed image using different algorithms, in accordance with an embodiment of the present disclosure.

FIG. 6, with reference to FIGS. 1 through 5, shows a reconstructed image using different algorithms, in accordance with an embodiment of the present disclosure. As can be clearly seen, the model-based MWI (e.g., the method of the present disclosure) showed better tumor localization by suppressing the unwanted clutter. Here for the sake of illustration, the system 100 and the method of the present disclosure only provided for two instances, however a similar performance in all other instances can be expected. This improvement with the model-based MWI approach (e.g., the method of the present disclosure) can be attributed for taking into account the kernel unlike the other conventional techniques which use only time delay.

Intelligent Scanning Versus Uniform Scanning:

The system 100 and the method of the present disclosure provide results to demonstrate the advantage of intelligent scanning against a uniform set of measurements using the model-based MWI algorithm (e.g., the method of the present disclosure). The RL agent as implemented by the system 100 was trained with the data sampled from the replay buffer using the DDQN architecture shown in FIG. 5. Reward for the RL agent at any given state $S_t$ was computed by using the MSE of the reconstructed DAS microwave image ($S_t$) with the ground truth DAS image (GT) obtained using all the 72 measurements. Since, RL based scanning requires to compute MWI (state) of the scene for each action, the system 100 employed DAS in its implementation and only at the end of episode use the method of the present disclosure. Instead of DAS, one can also use the method of the present disclosure for state determination. During experiments, the system 100 and the method of the present disclosure have found that the tumor location plays a key role in optimal action determination (refer FIG. 7(C)) and the impact is found to be minimal between using model-based MWI and DAS. Since DAS is faster compared to other algorithms, the system 100 used DAS only for state determination. DDQN used a replay buffer size of 20000 similar to conventional literature (e.g., refer "L. Pineda, S. Basu, A. Romero, R. Calandra, and M. Drozdzal, "Active mr k-space sampling with reinforcement learning," in Medical Image Computing and Computer Assisted Intervention-MICCAI 2020: $23^{rd}$ International Conference, Lima, Peru, Oct. 4-8, 2020, Proceedings, Part II 23. Springer, 2020, pp. 23-33.") and discount factor $\gamma$ was set to 0.99. The DDQN was trained for 2.3M transition steps to learn the optimum policy for any given state.

Figures 7A, 7B, 7C:
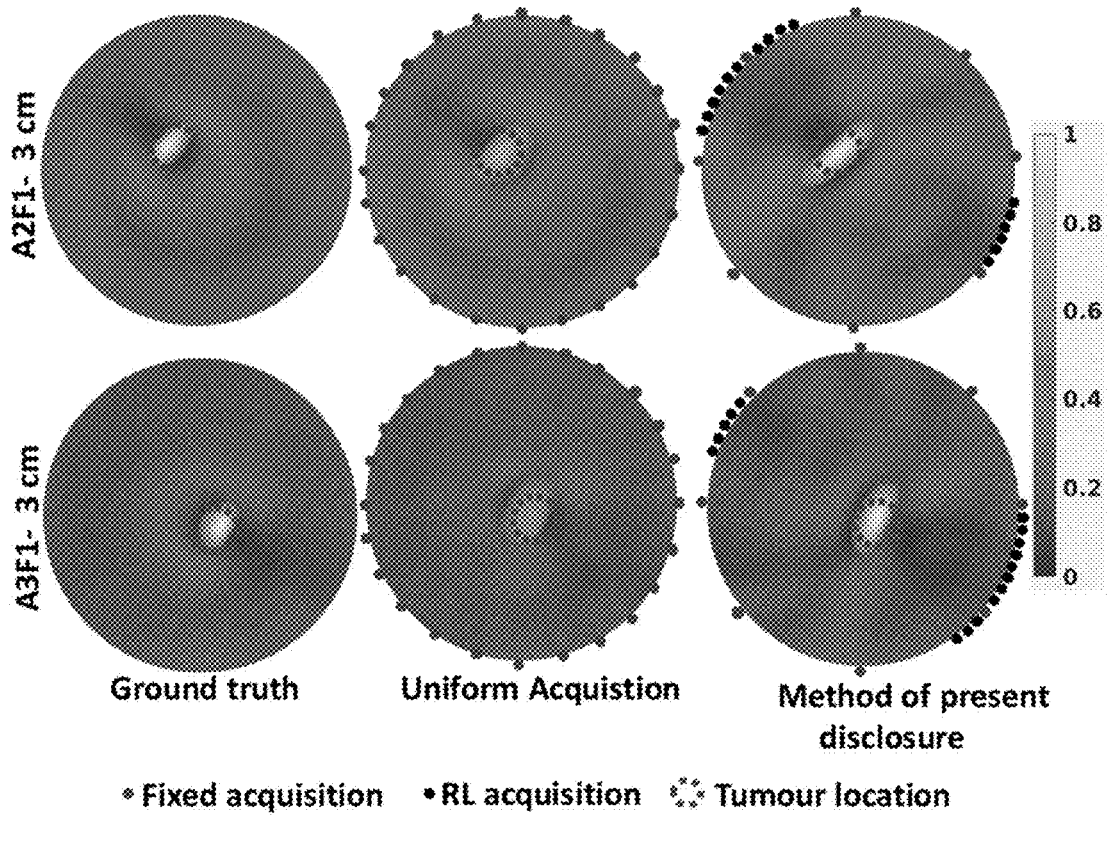
FIGS. 7A through 7C show visual MWI obtained using all 72 measurements, using only 24 uniform spaced fixed measurements and the method of the present disclosure using reinforcement learning (RL) acquisition with $N_a$=24 respectively, in accordance with an embodiment of the present disclosure.

As described earlier, the system 100 and the method of the present disclosure have fixed the maximum number of acquisitions $N_a$=24, out of which the initial $N_u$=8 scans were done uniformly. The RL agent then intelligently picked the antenna locations for the remaining $N_a-N_u$=16 locations. FIGS. 7A through 7C, with reference to FIGS. 1 through 6, show visual MWI obtained using all 72 measurements, using only 24 uniform spaced fixed measurements and the method of the present disclosure using reinforcement learning (RL) acquisition with $N_a$=24 respectively, in accordance with an embodiment of the present disclosure. It is to be observed from FIG. 7B that using only uniform measurements results in poorer tumor localization. However, with the method of the present disclosure, it is clearly evident that the tumor localization has improved significantly. FIG. 7C also shows the measurement locations suggested by the RL agent from which it is important to notice that more measurements are intelligently taken around the tumor which resulted in this improvement.

Figure 8:
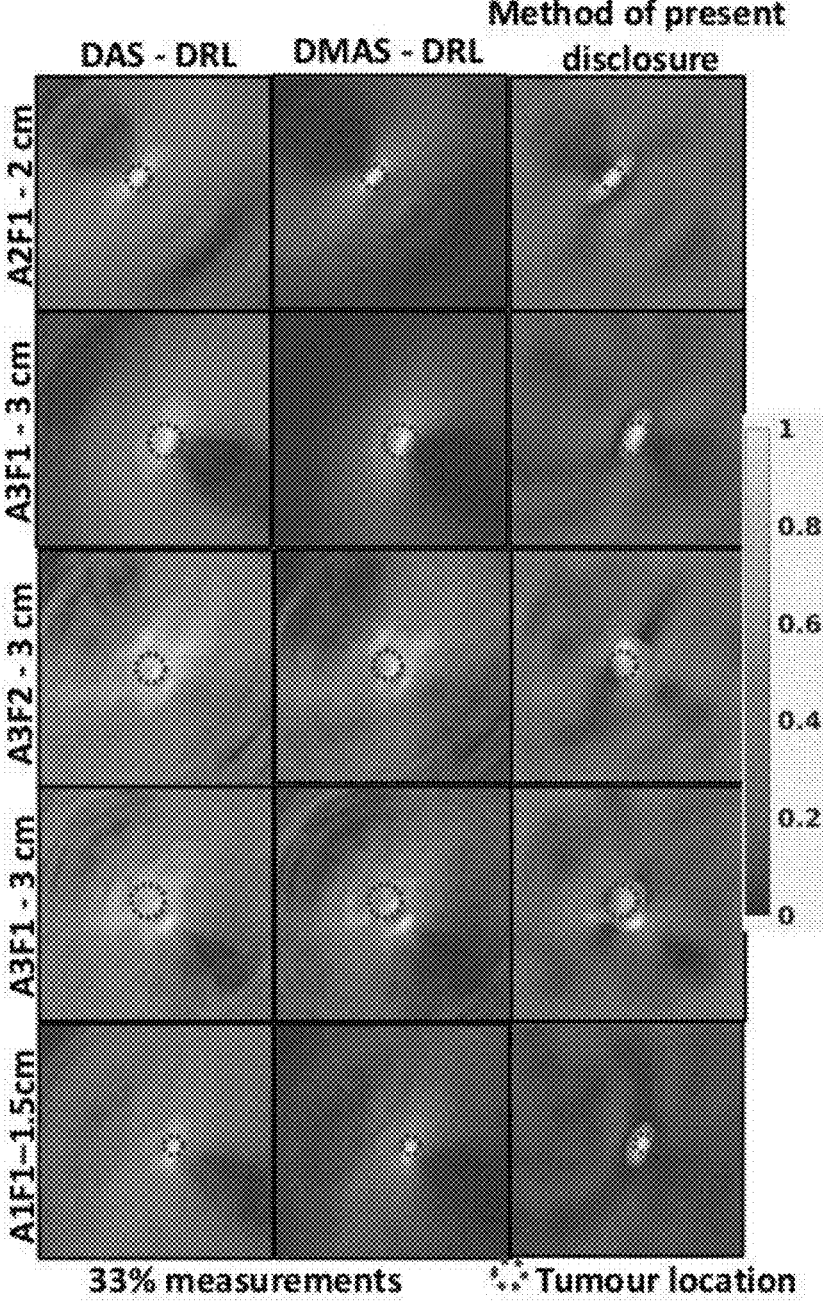
FIG. 8 shows visual comparison of the method of the present disclosure against Delay-And-Sum-Deep RL (DAS-DRL) and Delay-Multiply-and-Sum-Deep RL (DMAS-DRL), in accordance with an embodiment of the present disclosure.

The system 100 further provides the quantitative and qualitative comparison of the and method of the present disclosure against other techniques. The intelligently scanned radar measurements from $N_a$=24 locations were fed to different algorithms such as DAS, DMAS and model-based MWI to reconstruct the corresponding MWI indicated as DAS-RL, DMAS-RL and the and method of the present disclosure respectively. For visual comparison, the system 100 provides 5 test cases as shown in FIG. 8. More specifically, FIG. 8, with reference to FIGS. 1 through 7C, shows visual comparison of the method of the present disclosure against Delay-And-Sum-Deep RL (DAS-DRL) and Delay-Multiply-and-Sum-Deep RL (DMAS-DRL), in accordance with an embodiment of the present disclosure. It is to be noted that the system 100 has used only 24 measurements for reconstruction. As observed in all the cases, the method of the present disclosure showed improved tumor localization with better clutter suppression. Further, Signal to Mean Ratio (SMR) used in conventional technique (e.g., refer "T. Reimer et. al") has been used as a metric to evaluate MWI reconstruction performance. SMR is defined as:

$$SMR = 20\log_{10}\frac{S_{max}}{C_{mean}} \quad (8)$$

where $S_{max}$ is defined as maximum intensity in the tumor region (area within the red circle) and $C_{mean}$ is defined as the mean of the intensity in the clutter region (area outside the red circle). Average SMR values for 20 test cases is shown in Table 1, where the first row shows the different algorithms such as DAS, DMAS and model-based MWI using uniform scanning and the second row shows the same using RL based scanning.

TABLE 1

| | SMR metric in decibel (dB) | | |
| --- | --- | --- | --- |
| Scanning | DAS | DMAS | Model-based MWI (method of the present disclosure) |
| Uniform | 7.6 | 14.7 | 28.2 |
| RL agent | 9.2 | 17.1 | 31.0 |

As observed RL based scanning has shown improved SMR metric for all the MWI algorithms. Further, DMAS performed better than DAS in terms of clutter suppression and a performance improvement of close to 2× (2 times) can be observed with the model-based MWI (method of the present disclosure).

The results thus showed that the Model-based MWI (method of the present disclosure) which comprises of the efficient model-based MWI reconstruction, and the intelligent RL based scanning system outperforms the existing techniques by a factor of 2× (2 times). Furthermore, only a minimal deterioration is observed despite using only 33% of the total measurements as compared to using full measurements.

An enhanced MWI system (e.g., the system 100) which comprises of an efficient model-based reconstruction algorithm and an RL based intelligent scanning mechanism is described in the present disclosure. The reconstruction algorithm is framed as an inverse problem which is solved by imposing sparsity prior. A DRL based intelligent scanning is implemented by the system 100 to optimally choose the radar locations for a quicker scan. The reconstruction performance of method of the present disclosure has been compared with other conventional methods using an open dataset and close to 2×SMR improvement has been obtained against other conventional techniques. Furthermore, the visual results also demonstrate a negligible deterioration for the method of the present disclosure in spite of using only 33% of total measurements compared to using full set of measurements.

Thus, the system 100 and the method of the present disclosure overcome the limitations of the existing MWI approaches and provide improved tumor reconstruction with reduced scan duration. This makes it an attractive breast tumor screening system that can help to extend the detection process from clinics to anywhere.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:

obtaining, via one or more hardware processors, an initial coarse microwave (MW) data pertaining to a set of predefined uniform locations scanned around a specific portion of a body of a subject;

sequentially recommending, by using a trained reinforcement learning (RL) agent, via the one or more hardware processors, one or more subsequent locations pertaining to the specific portion of the body of the subject using the initial coarse microwave data to obtain a set of subsequent MW data;

vectorizing and stacking, via the one or more hardware processors, the initial coarse microwave data and the set of subsequent MW data to obtain a measurement matrix;

estimating, via the one or more hardware processors, a Kernel K using a reference point scatterer of dielectric value $\varepsilon_0$ and an area $A_r$ at a set of reference coordinate placed in a region of interest, wherein the Kernel K estimated at the set of reference coordinate is used to estimate the Kernel K at remaining coordinates in the region of interest based on an Euclidean distance between the set of reference coordinate and the remaining coordinates; and estimating, via the one or more hardware processors, an unknown dielectric constant of the region of interest in the specific portion using an inverse model formulation obtained from the measurement matrix and the Kernel K, wherein the unknown dielectric constant indicates a degree of severity of a disease associated with the region of interest in the specific portion of body tissue;

wherein the MW data comprises MW radiation.

2. The processor implemented method of claim 1, wherein the trained reinforcement learning (RL) agent is obtained by:

defining a state set, an action set, an environment, and a reward pertaining to acquisition of MW data, wherein the state set is defined by a set of reconstructed MW images that is used by the RL agent to select an action, wherein an initial state obtained from an initial coarse MW data enables the RL agent to select an optimal action from the action set, wherein the action set comprises a set of positions from which the set of subsequent MW data is acquired, wherein MW data pertaining to a specific action is collected based on a location being recommended, the environment reconstructs a next state of the region of interest based on the MW data collected from a set of cumulative actions selected by the RL agent, wherein a reward is computed by comparing a current state with a ground truth state obtained by using an entire MW data obtained from a plurality of possible acquisition positions, and wherein the current state, the action, the next state, and the reward constitutes a replay memory buffer data being stored in the replay memory buffer;

randomly sampling data amongst the replay memory buffer data stored in a replay memory buffer to obtain sampled data;

computing a mean square error (MSE) loss using the randomly sampled data based on a pre-defined equation (Bellman equation);

training one or more network parameters of a Double Deep Q Network (DDQN), wherein the DDQN serves as the trained RL agent, wherein during the training, the MSE loss serves as feedback to the RL agent for a given-state-action pair; and deploying the trained RL agent in the environment for scanning to obtain one or more optimal action indices required for estimating the unknown dielectric constant.

3. The processor implemented method of claim 1, wherein the step of training the one or more network parameters of the DDQN is preceded by:

receiving a MW image;

generating a value function for one or more action sets based on the MW image; and selecting at least one action from the one or more action sets based on an associated maximum value function.

4. The processor implemented method of claim 1, wherein a dielectric constant and an area of a first type of cells and a second type of cells in the region of interest are different from each other, wherein the unknown dielectric constant of the region of interest estimated uses a sparsity constraint, which is based on the dielectric constant and the area, and wherein the unknown dielectric constant of the region of interest is estimated using an iterative threshold technique.

5. The processor implemented method of claim 1, wherein number of MW data to be acquired for an episode is based on a scanning duration, and wherein the scanning duration is one of a pre-determined duration or an empirically determined duration.

6. The processor implemented method of claim 1, wherein the region of interest comprises a tissue.

7. A system, comprising:

a memory storing instructions;

one or more communication interfaces; and one or more hardware processors coupled to the memory via the one or more communication interfaces, wherein the one or more hardware processors are configured by the instructions to:

obtain an initial coarse microwave (MW) data pertaining to a set of predefined uniform locations scanned around a specific portion of a body of a subject;

sequentially recommend, by using a trained reinforcement learning (RL) agent, one or more subsequent locations pertaining to the specific portion of the body of the subject using the initial coarse microwave data to obtain a set of subsequent MW data;

vectorize and stack the initial coarse microwave data and the set of subsequent MW data to obtain a measurement matrix;

estimate a Kernel K using a reference point scatterer of dielectric value $\varepsilon_0$ and an area $A_r$ at a set of reference coordinate placed in a region of interest, wherein the Kernel K estimated at the set of reference coordinate is used to estimate the Kernel K at remaining coordinates in the region of interest based on an Euclidean distance between the set of reference coordinate and the remaining coordinates; and estimate an unknown dielectric constant of the region of interest in the specific portion using an inverse model formulation obtained from the measurement matrix and the Kernel K, wherein the unknown dielectric constant indicates a degree of severity of a disease associated with the region of interest in the specific portion of the body tissue;

wherein the MW data comprises MW radiation.

8. The system of claim 7, wherein the trained reinforcement learning (RL) agent is obtained by:

defining a state set, an action set, an environment, and a reward pertaining to acquisition of MW data, wherein the state set is defined by a set of reconstructed MW images that is used by the RL agent to select an action, wherein an initial state obtained from an initial coarse MW data enables the RL agent to select an optimal action from the action set, wherein the action set comprises a set of positions from which the set of subsequent MW data is acquired, wherein MW data pertaining to a specific action is collected based on a location being recommended, the environment reconstructs a next state of the region of interest based on the MW data collected from a set of cumulative actions selected by the RL agent, wherein a reward is computed by comparing a current state with a ground truth state obtained by using an entire MW data obtained from a plurality of possible acquisition positions, and wherein the current state, the action, the next state, and the reward constitutes a replay memory buffer data being stored in the replay memory buffer;

randomly sampling data amongst the replay memory buffer data stored in a replay memory buffer to obtain sampled data;

computing a mean square error (MSE) loss using the randomly sampled data based on a pre-defined equation (Bellman equation);

training one or more network parameters of a Double Deep Q Network (DDQN), wherein the DDQN serves as the trained RL agent, wherein during the training, the MSE loss serves as feedback to the RL agent for a given-state-action pair; and deploying the trained RL agent in the environment for scanning to obtain one or more optimal action indices required for estimating the unknown dielectric constant.

9. The system of claim 8, wherein prior to training the one or more network parameters of the DDQN, the one or more hardware processors are further configured by the instructions to:

receive a MW image;

generate a value function for one or more action sets based on the MW image; and select at least one action from the one or more action sets based on an associated maximum value function.

10. The system of claim 7, wherein a dielectric constant and an area of a first type of cells and a second type of cells in the region of interest are different from each other, wherein the unknown dielectric constant of the region of interest estimated uses a sparsity constraint, which is based on the dielectric constant and the area, and wherein the unknown dielectric constant of the region of interest is estimated using an iterative threshold technique.

11. The system of claim 7, wherein number of MW data to be acquired for an episode is based on a scanning duration, and wherein the scanning duration is one of a pre-determined duration or an empirically determined duration.

12. The system of claim 7, wherein the region of interest comprises a tissue.

13. One or more non-transitory machine-readable information storage mediums comprising one or more instructions which when executed by one or more hardware processors cause:

obtaining an initial coarse microwave (MW) data pertaining to a set of predefined uniform locations scanned around a specific portion of a body of a subject;

sequentially recommending, by using a trained reinforcement learning (RL) agent, one or more subsequent locations pertaining to the specific portion of the body of the subject using the initial coarse microwave data to obtain a set of subsequent MW data;

vectorizing and stacking the initial coarse microwave data and the set of subsequent MW data to obtain a measurement matrix;

estimating a Kernel K using a reference point scatterer of dielectric value $\varepsilon_0$ and an area $A_r$ at a set of reference coordinate placed in a region of interest, wherein the Kernel K estimated at the set of reference coordinate is used to estimate the Kernel K at remaining coordinates in the region of interest based on an Euclidean distance between the set of reference coordinate and the remaining coordinates; and estimating an unknown dielectric constant of the region of interest in the specific portion using an inverse model formulation obtained from the measurement matrix and the Kernel K, wherein the unknown dielectric constant indicates a degree of severity of a disease associated with the region of interest in the specific portion of body tissue;

wherein the MW data comprises MW radiation.

14. The one or more non-transitory machine-readable information storage mediums of claim 13, wherein the trained reinforcement learning (RL) agent is obtained by:

defining a state set, an action set, an environment, and a reward pertaining to acquisition of MW data, wherein the state set is defined by a set of reconstructed MW images that is used by the RL agent to select an action, wherein an initial state obtained from an initial coarse MW data enables the RL agent to select an optimal action from the action set, wherein the action set comprises a set of positions from which the set of subsequent MW data is acquired, wherein MW data pertaining to a specific action is collected based on a location being recommended, the environment reconstructs a next state of the region of interest based on the MW data collected from a set of cumulative actions selected by the RL agent, wherein a reward is computed by comparing a current state with a ground truth state obtained by using an entire MW data obtained from a plurality of possible acquisition positions, and wherein the current state, the action, the next state, and the reward constitutes a replay memory buffer data being stored in the replay memory buffer;

randomly sampling data amongst the replay memory buffer data stored in a replay memory buffer to obtain sampled data;

computing a mean square error (MSE) loss using the randomly sampled data based on a pre-defined equation (Bellman equation);

training one or more network parameters of a Double Deep Q Network (DDQN), wherein the DDQN serves as the trained RL agent, wherein during the training, the MSE loss serves as feedback to the RL agent for a given-state-action pair; and deploying the trained RL agent in the environment for scanning to obtain one or more optimal action indices required for estimating the unknown dielectric constant.

15. The one or more non-transitory machine-readable information storage mediums of claim 13, wherein the step of training the one or more network parameters of the DDQN is preceded by:

receiving a MW image;

generating a value function for one or more action sets based on the MW image; and selecting at least one action from the one or more action sets based on an associated maximum value function.

16. The one or more non-transitory machine-readable information storage mediums of claim 13, wherein a dielectric constant and an area of a first type of cells and a second type of cells in the region of interest are different from each other, wherein the unknown dielectric constant of the region of interest estimated uses a sparsity constraint, which is based on the dielectric constant and the area, and wherein the unknown dielectric constant of the region of interest is estimated using an iterative threshold technique.

17. The one or more non-transitory machine-readable information storage mediums of claim 13, wherein number of MW data to be acquired for an episode is based on a scanning duration, and wherein the scanning duration is one of a pre-determined duration or an empirically determined duration.

18. The one or more non-transitory machine-readable information storage mediums of claim 13, wherein the region of interest comprises a tissue.

* * * * *